US009579055B1

(12) United States Patent
Rood et al.

(10) Patent No.: US 9,579,055 B1
(45) Date of Patent: Feb. 28, 2017

(54) APPARATUS FOR NON-INVASIVE FETAL BIOSIGNAL ACQUISITION

(75) Inventors: Aaron T. Rood, Rocky River, OH (US); Greg S. Shaw, University Heights, OH (US); Jessica M. Moore, Brunswick, OH (US); Douglas Wajda, Farmdale, OH (US)

(73) Assignee: Orbital Research Inc., Cleveland, OH (US)

( * ) Notice: Subject to any disclaimer, the term of this patent is extended or adjusted under 35 U.S.C. 154(b) by 2504 days.

(21) Appl. No.: 12/253,430

(22) Filed: Oct. 17, 2008

(51) Int. Cl.
*A61B 5/04* (2006.01)
*A61B 5/00* (2006.01)
*A61B 5/0444* (2006.01)

(52) U.S. Cl.
CPC .......... *A61B 5/4362* (2013.01); *A61B 5/0444* (2013.01)

(58) Field of Classification Search
CPC .. A61B 5/0444; A61B 5/4362; A61B 5/02411
USPC .................................................. 600/389, 511
See application file for complete search history.

(56) References Cited

U.S. PATENT DOCUMENTS

| 3,348,548 A * | 10/1967 | Chardack ..................... 607/122 |
| 3,703,168 A | 11/1972 | Frink |
| 4,781,200 A * | 11/1988 | Baker ........................... 600/483 |
| 5,372,139 A | 12/1994 | Holls et al. |
| 6,115,624 A * | 9/2000 | Lewis et al. .................. 600/376 |
| 6,151,520 A * | 11/2000 | Combs .......................... 600/376 |
| 6,751,498 B1 | 6/2004 | Greenberg et al. |
| 6,816,744 B2 * | 11/2004 | Garfield et al. .............. 600/546 |
| 7,032,302 B1 * | 4/2006 | Schmidt et al. ................. 29/825 |
| 7,245,957 B2 * | 7/2007 | Rowe et al. ................... 600/391 |
| 8,032,210 B2 | 10/2011 | Finneran et al. |
| 2003/0045787 A1 | 3/2003 | Shulze et al. |
| 2005/0261564 A1 | 11/2005 | Ryu et al. |
| 2005/0267376 A1 | 12/2005 | Marossero et al. |
| 2005/0267377 A1 | 12/2005 | Marossero et al. |
| 2005/0277841 A1 * | 12/2005 | Shennib ........................ 600/511 |
| 2007/0078324 A1 | 4/2007 | Wijisiriwardana |
| 2009/0259133 A1 * | 10/2009 | Wolfberg et al. ............. 600/511 |

* cited by examiner

*Primary Examiner* — Christopher D Koharski
*Assistant Examiner* — Philip C Edwards
(74) *Attorney, Agent, or Firm* — Brian Kolkowski

(57) ABSTRACT

An apparatus for measuring biopotential signals comprises a plurality of electrodes embedded or affixed to a wearable worn about the torso of a pregnant subject, enabling the non-invasive acquisition of electrocardiographic signals and the extraction of separate fetal and maternal electrocardiographic signals therefrom. The wearable is stretchable or adjustable to accommodate any maternal body habitus and can advantageously employ dry physiologic electrodes to eliminate the step of skin preparation and provide longer-term monitoring that is also both more convenient and more comfortable.

10 Claims, 4 Drawing Sheets

APPARATUS FOR NON-INVASIVE FETAL BIOSIGNAL ACQUISITION

TECHNICAL FIELD

The present invention relates to diagnostic or monitoring medical apparatus, and more particularly, to apparatus for monitoring the electrophysiological signals of fetuses and expectant mothers.

BACKGROUND

Acquiring signals indicative of the health of a fetus, both during gestation and during labor, assists in the treatment of a pregnant subject to insure healthy growth and delivery of the fetus. A determination of the heart health profile of a fetus may be used to screen for developmental heart defects, and, as fetal hypoxemia can alter the shape of the fetal electrocardiogram (fECG) waveform, the ability to acquire the electrocardiogram of a fetus is particularly desirable during labor to determine whether the fetus is getting enough oxygen. Such information assists an obstetrician in making informed health care decisions, such as whether to expedite delivery by means such as Caesarian section, in order to prevent or reduce the risk of severe metabolic acidosis and neonatal encephalopathy, which can result in cerebral palsy or other undesirable outcomes. Reliable acquisition of fetal ECG signals is critical to the identification of characteristic ECG patterns that detect existent fetal injury or predict impending or fetal injury caused by inflammatory, hypoxic, or ischemic insults. Presently-used invasive methods for fetal ECG monitoring are only conducted during labor, so there exists no ECG method of screening for fetal heart defects. Earlier, more accurate determination of such defects might lead to quicker repair of such defects after birth, or even before birth.

Non-invasive acoustic devices such as stethoscopes and microphones have long been used to determine fetal heart rate by listening for and counting a fetal heartbeat. Such methods do not present all the information found in a fetal electrocardiogram. Devices such as the cardiotocograph and the Doppler fetal monitor use an ultrasound transducer to detect fetal heartbeat and determine fetal heart rate, but such devices are labor intensive and inherently unreliable because they require regular adjustment of an ultrasound transducer over a fetal artery or heart valve, such placement being prone to change due to fetal or maternal movement. In any case, these devices do not acquire an electrocardiogram.

The fetal scalp electrode method involves passing an electrode through the pregnant subject's cervix and attaching it to the head of the fetus. Use of such a method is limited to the final stages of labor when the fetal scalp is accessible through the birth canal following the rupture of the amniotic membranes and the dilation of the cervix, and moreover presents the disadvantages typical of invasive diagnostics, e.g., complexity and expense of setup, subject discomfort, potential for harm to the fetus, and risk of infection. Cases of fetal scalp abscess have been reported after use of this method.

Although an accurate model of fetal heart activity can be constructed, the acquisition of a true representation of a fetal ECG from electrophysiological signals acquired by electrodes non-invasively placed on the skin of the maternal torso is impeded by absorptive media that exist between the fetus and the subject's abdominal surface and by the presence of the stronger maternal ECG that must be filtered out to remove interference. Techniques for isolating the fetal cardiac signal have remained as simple as template subtraction, matched filters, averaging and principal component analysis (PCA).

Experimental non-invasive fetal electrophysiology monitoring systems are cumbersome because of the setup time involved in the placement of the electrodes. NeuroDimensions Incorporated has been developing fECG algorithms, and has used 8-12 gel-based ECG electrodes for their acquisition apparatus. This number of ECG electrodes is inadequate to permit acquisition of ECG signals in a sufficient number of electrical axes so as to extract and distinguish fetal ECG and maternal ECG from the acquired signal. The portable fetal heart rate monitoring system CARE 2000, developed by Monica Healthcare, records the very small electrical signals generated by the fetal heartbeat and other electrophysiological events present on the maternal abdomen. The Care 2000 has demonstrated excellent correlation of the extracted fetal heart rate in comparison with conventional Doppler ultrasound fetal heart recording. The electrophysiological signals can also be used to extract fetal position, uterine activity information, and fetal ECG morphology parameters. However, this device cannot identify or assess the entire ECG waveform.

U.S. Pat. No. 3,703,168 to Frink describes a plurality of surface electrodes attached to a mother's skin and signal processing apparatus for distinguishing fetal rhythm ECG. U.S. Pat. No. 4,781,200 to Baker describes mounting a plurality of acoustic sensors and a movement sensor to a belt for detecting fetal heart rate, and while the disclosure contemplates using electrocardiographic electrodes in lieu of acoustic sensors, it does not envision acquiring a fetal electrocardiogram, only using sensors to obtain fetal heart rate. Baker also does not envision extraction and distinction of various types of electrophysiological signals from each other, such as ECG from a signal dominated by EMG, or vice versa.

Gel-type electrodes include a hydrating gel for reducing impedance of electrode-skin contact. Because this impedance increases as the hydrating gel dries, ultimately to the point where artifact dominates useful electrophysiological signal, these electrodes have a limited shelf life and a relatively short useful lifetime once applied. Application of gel-type electrodes also typically involves preparation of the electrode placement site by emery abrasion of the stratum corneum layer of the skin. For this reason and because of the adhesives typically used to secure them to the skin site, gel-type electrodes are generally not repositionable after they have been placed. They can become uncomfortable after extended wear due to the skin abrasion and due to irritation caused by the tape.

It is therefore the object of the present invention to offer a comfortable, convenient, wearable monitoring apparatus that makes both short-term and long-term non-invasive fetal and maternal biosignal monitoring simple and inexpensive. Specifically, it would be desirable to have a monitoring apparatus that could be easily put on and taken off without special training that would nevertheless be capable of reliably acquiring high-quality electrophysiological signals from both the fetus and the mother. Additionally, it is the object of the present invention to offer an electrode harness in the form of a wearable with sensor design and placement adapted to the acquisition of fetal and maternal ECG signals. Additionally, it is the object of the present invention to provide a method of fetal ECG acquisition useable at any stage of gestation or delivery. It is further the object of the present invention to offer an integrated, resizable electrode harness that uses dry electrodes with an unlimited shelf life and a much longer useful lifetime once applied, and which also reduces setup time by eliminating the need for skin preparation. Finally, it is the object of the present invention to offer an electrode harness that allows advanced assessment of the fetal ECG waveform characteristics, which will mitigate risk to the fetus during delivery.

SUMMARY

The present invention relates to an electrode harness and more particularly to an electrode harness with various features that enhance the use and performance of the electrode harness. The present invention further relates to a method of taking biopotential measurements. These biopotential measurements may include fetal electrocardiogram (fECG), which in this disclosure refers to an electrical signal that is substantially free of the corrupting signal corresponding to the electrical activity of the heart of the mother, and may include maternal electrocardiogram (mECG).

The electrode harness and methods of the present invention allow for use with most applications where biopotential measurements are taken. The electrode harness can be used in ECG, EEG, EMG, and other such biopotential measurement applications, and may also have the ability to distinguish fECG from maternal signals other than mECG. Because of the versatility of various embodiments of the present invention, preferably the electrode harness can be adjusted for different applications or for application to various sized and shaped subjects. The electrode harness is further preferably part of a system, which includes either wireless or tethered bridges between the electrode harness and a monitor, and preferably includes various forms of processors for analyzing the biopotential signal.

The electrode harness of the present invention overcomes one or more of the significant drawbacks of other electrode systems. One of the features of various embodiments of the present invention includes a harness with lockable or non-releasable connectors, which allows for disposal or removal of the electrode harness and electrodes in one piece. This prevents clutter, and, more importantly, medical waste by reducing the possibility that the electrodes separate from the harness. Another feature of the electrode harness of various embodiments of the present invention is partial or full shielding of the electrical pathways of the harness from electrical noise. Finally, another significant feature of the electrode harness of various embodiments of the present invention is the use of an electrode harness containing one or more dry electrodes.

In one embodiment, the present invention includes an apparatus for non-invasively acquiring the electrocardiogram of a fetus comprising a wearable worn about a torso of a pregnant subject, a plurality of dry electrodes affixed to or embedded in the wearable, and a plurality of connectors providing an electrical pathway from each of the plurality of dry electrodes wherein the dry electrodes are capable of being connected to an electronic device capable of modifying and/or re-transmitting electrical signals or modified electrical signals received from the plurality of dry electrodes. Preferably, the electronic device or a different electronic device is capable of differentiating between the maternal ECG and the fetal ECG.

In another embodiment, the present invention includes an apparatus for non-invasively acquiring the electrocardiogram of a fetus comprising a wearable worn about a torso of a pregnant subject, a plurality of dry electrodes affixed to or embedded in the wearable, and a plurality of connectors providing an electrical pathway from each of the plurality of dry electrodes wherein the dry electrodes are capable of being connected to an electronic device capable of modifying and/or re-transmitting electrical signals or modified electrical signals received from the plurality of dry electrodes. Preferably, the electronic device or a different electronic device is capable of differentiating between the maternal ECG and the fetal ECG.

In yet another embodiment, the present invention includes an apparatus for non-invasively acquiring the electrocardiogram of a fetus comprising a wearable worn about a torso of a pregnant subject, a plurality of dry electrodes affixed to or embedded in the wearable, each of the dry electrodes having a stiffener for positioning the dry electrode to better contact the subject's skin, and a plurality of connectors providing an electrical pathway from each of the plurality of dry electrodes wherein the dry electrodes are capable of being connected to an electronic device capable of modifying and/or re-transmitting electrical signals or modified electrical signals received from the plurality of dry electrodes. Preferably, the electronic device or a different electronic device is capable of differentiating between the maternal ECG and the fetal ECG.

In still another embodiment, the present invention includes an apparatus for non-invasively acquiring the electrocardiogram of a fetus comprising a wearable worn about a torso of a pregnant subject, a plurality of dry electrodes affixed to or embedded in the wearable, a ring for attaching a dry electrode, the ring providing stiffness to position the dry electrode to better contact the subject's skin, and a plurality of connectors providing an electrical pathway from each of the plurality of dry electrodes wherein the dry electrodes are capable of being connected to an electronic device capable of modifying and/or re-transmitting electrical signals or modified electrical signals received from the plurality of dry electrodes. Preferably, the electronic device or a different electronic device is capable of differentiating between the maternal ECG and the fetal ECG.

In yet another embodiment, the present invention includes an apparatus for non-invasively acquiring the electrocardiogram of a fetus comprising a wearable worn about the torso of a pregnant subject, a plurality of dry electrodes affixed to or embedded in the wearable, and a plurality of connectors providing an electrical pathway from each of the plurality of dry electrodes wherein the dry electrodes are capable of being connected to an electronic device capable of modifying and/or re-transmitting electrical signals or modified electrical signals received from the plurality of dry electrodes. Preferably, the electronic device or a different electronic device is capable of differentiating between the maternal ECG and the fetal ECG.

In still another embodiment, the present invention includes an apparatus for non-invasively acquiring the electrocardiogram of a fetus comprising a wearable worn about a torso of a pregnant subject, the torso having a front, a back, and two sides, a plurality of dry electrodes affixed to or embedded in the wearable, such that the wearable when properly worn positions at least two dry electrodes on each of the sides, the back, and the front of the torso of the subject, and a plurality of connectors providing an electrical pathway from each of the plurality of dry electrodes wherein the dry electrodes are capable of being connected to an electronic device capable of modifying and/or re-transmitting electrical signals or modified electrical signals received from the plurality of dry electrodes. Preferably, the electronic device or a different electronic device is capable of differentiating between the maternal ECG and the fetal ECG.

In yet another embodiment, the present invention includes an apparatus for non-invasively acquiring the electrocardiogram of a fetus comprising a wearable worn about a torso of a pregnant subject, the torso having a front, a back, and two sides, a plurality of dry electrodes affixed to or embedded in the wearable, such that the wearable when properly worn positions at least one dry electrode on each of the sides, the back, and the front of the torso of the subject, and a plurality of connectors providing an electrical pathway from each of the plurality of dry electrodes wherein the dry electrodes are capable of being connected to an electronic device capable of modifying and/or re-transmitting electrical signals or modified electrical signals received from the plurality of dry electrodes. Preferably, the electronic device or a different electronic device is capable of differentiating between the maternal ECG and the fetal ECG.

In yet other embodiments, the present invention includes an apparatus for non-invasively acquiring the electrocardiogram of a fetus comprising a wearable worn about a torso of a pregnant subject, the torso having a back, a front, and two sides, a plurality of electrodes affixed to or embedded in the wearable, such that the wearable when properly worn positions the electrodes with appropriate spacing and positioning so as to be capable of acquiring a set of electrophysiological signals in a sufficient number of electrical axes such that a fetal ECG signal and/or a maternal ECG signal may be extracted from the acquired electrophysiological signals.

In still other embodiments, the present invention includes an apparatus for non-invasively acquiring an electrophysiological signal of interest comprising a wearable worn about a torso or limb of a subject, a plurality of electrodes affixed to or embedded in the wearable, such that the wearable when properly worn positions the electrodes with appropriate spacing and positioning so as to be capable of acquiring a set of electrophysiological signals in a sufficient number of electrical axes such that one or multiple electrophysiological signals of interest may be extracted from the acquired electrophysiological signals.

The present invention is intended to monitor fetal ECG, maternal ECG, contractions, and other biophysical markers that provide information about the health status of the subject, the fetus, or both. The present invention may be used to monitor the subject and/or fetus during gestation, before or during labor, immediately after labor, during high-risk activities, at home, during routine doctor visits, and during ambulance transports or other ambulatory activities. The apparatus of the present invention may be worn continuously, for hours, days, weeks, or even months.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

DESCRIPTION OF THE PREFERRED EMBODIMENTS

Figure 1:
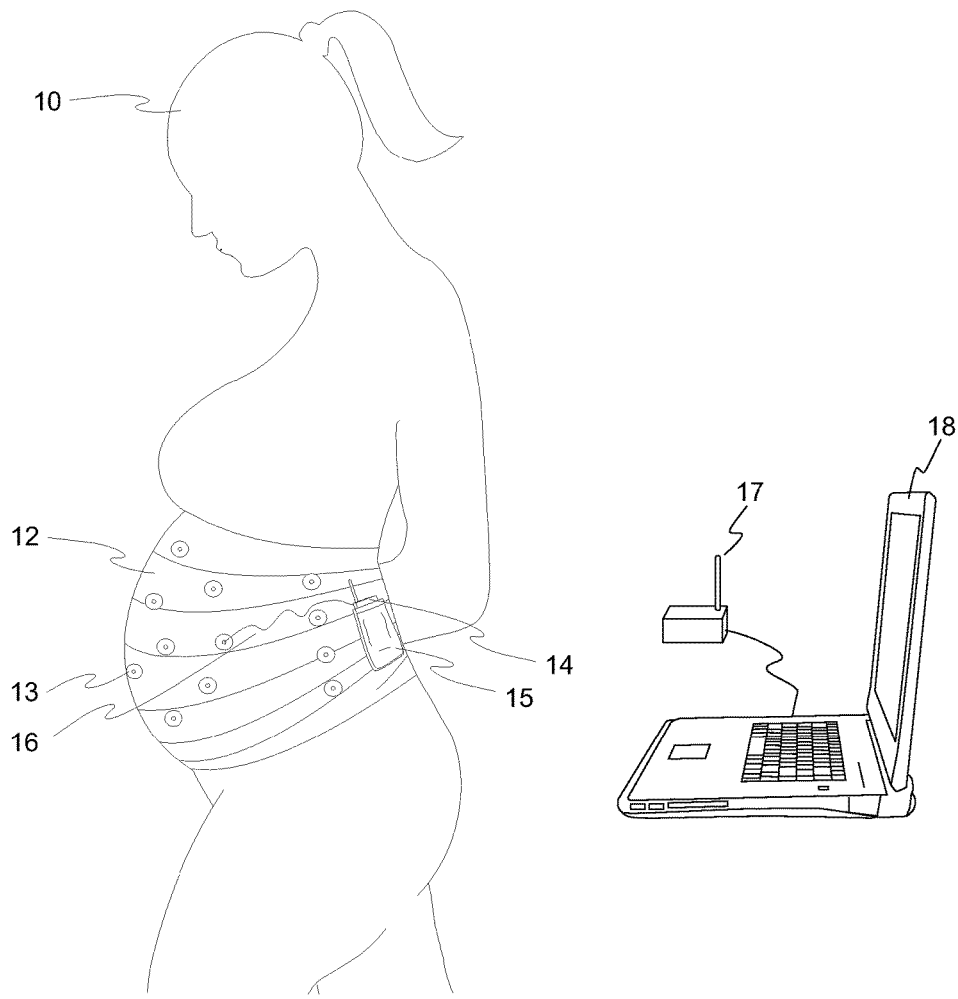
FIG. 1. Schematic view of a subject wearing a biopotential measurement system with one embodiment of the electrode harness of the present invention.

The various embodiments of the electrode harness and methods of the present invention allow for use with most applications where biopotential or physiological measurements are taken. The electrode harness of the present invention is preferably used for sensing or detecting a physiological or biopotential signal from a subject, the subject being a human or other form of animal. Preferably, the subject is a pregnant human female. The electrode harness can be used in a variety of applications including but not limited to electrocardiography (ECG), electroencephalography (EEG), electrical impedance tomography (EIT), electromyography (EMG), electro-oculography (EOG), and bio-electrical impedance (BIA) biopotential or physiological measurement applications. Preferably the electrode harness can be stretched or adjusted to fit different various sized and shaped subjects, at all stages of gestation. The electrode harness is further preferably part of a system that includes either wireless or tethered connections between the electrode harness and a monitor, and preferably includes various forms of processors for analyzing the biopotential signal. The electrode harness of the present invention further allows for greater improvement in health care monitoring systems.

The electrode harness of the present invention preferably comprises a wearable (a belt, strap, tube, shirt, bra, gown, undergarment, high-waisted pant, or other garment or garment-like device) and a plurality of sensors affixed or embedded in the wearable. The material of the wearable may be single- or multi-layered or may be formed from a multi-layer laminate. The invention preferably contains at least one dry electrode and one or more additional sensors. Sensors may include, but are not limited to, gel-based electrodes, acoustic sensors, thermistors, accelerometers, pulse oximetry sensors, skin conductivity sensors, and sensors for signals corresponding to temperature, pulse rate, blood pressure, blood oxygenation or composition characterstics, or blood flow. The electrode harness of the present invention comprises at least 3 electrodes, and various embodiments may comprise different numbers of electrodes. In some embodiments, the electrode harness of the present invention comprises at least 5 electrodes. In other embodiments, the electrode harness of the present invention comprises at least 10 electrodes. In yet other embodiments, the electrode harness of the present invention comprises at least 20 electrodes. In still other embodiments, the electrode harness of the present invention comprises at least 32 electrodes. In yet other embodiments, the electrode harness of the present invention comprises at least 64 electrodes.

Importantly, the wearable is a single piece, so as to provide for easy use, and harnesses the electrodes such that the conformation of their placement relative to each other cannot be confused. As such, the wearable is not merely a wire mesh which could become tangled or placed on the body incorrectly, and nor does it comprise multiple pieces, which could be applied in an incorrect orientation or with incorrect relative spacing.

Preferably, the sensors are placed in an arrangement around the circumference of the subject's torso. The arrangement accommodates the sizing, body type, and dynamics of the pregnant subject for any body habitus. The arrangement may be linear, multiplanar, circular, or may include geometric arrays or matrices of sensors, or concentric rings of sensors. Sensors may be placed on the front, back, or sides of the torso in any combination. When properly worn about the torso of a pregnant subject, the sensors are advantageously arranged about the subject's torso to permit acquisition of maternal and fetal ECG in at least several electrical axes. The sensors may be permanently or semi-permanently secured to the wearable. This disclosure envisions any combination of permanently secured, semi-permanently secured, or removable sensors. Preferably, low-cost sensors, such as electrodes, may be permanently or semi-permanently secured to the wearable while high-cost sensors, such as acoustic sensors, may be easily removable from the wearable, providing for a disposable apparatus with non-disposable components that is easily and quickly set-up, and easily and quickly taken apart with only the high-cost, reusable sensors retained for subsequent re-use. Preferably, each of the sensors and the wearable may be disposable or reusable and may be used as a sterile or non-sterile device. Preferably, the wearable may be laundered with the sensors intact. Preferably, the wearable is not susceptible to failure from external water incursion. Preferably, the wearable is stain-resistant. Preferably, the wearable is made of non-allergenic materials.

In some embodiments of the present invention, the wearable is a tube or stretchable garment that is continuous and seamless and may be donned by sliding over the head or by stepping through. In other embodiments, the wearable is a strap or belt that may be adjustably resized and secured by mechanical or electrical closures including but not limited to hook and loop closures, buttons, snaps, buckles, latches, clasps, zippers, twists, hooks, magnets, electromagnets, or any other mechanical closure means known in the art. The base material of the wearable may be either elastic (stretchy) or non-elastic. The wearable may or may not contain latex. Preferably, the wearable is sizable to a range of body types and a range of gestational ages.

In some embodiments of the present invention, the electrodes or sensors embedded in or affixed to the wearable are connected via electrode leads or wires that are singly and individually attached to each electrode or sensor. The sensors may have a standard medical connector on one side, such as a snap or tab, making the electrical connection temporary, but in some embodiments may be hardwired, soldered, brazed, or welded, making the connection permanent. Preferably, the wearable contains the lead wires or other electrical components built-in or woven into the wearable. Such electrical components may include, but are not limited to, the data acquisition system, battery or other power supply, memory, and radio for transmitting acquired data. In embodiments of the present invention that use built-in electrode leads in the wearable, the electrode leads may be outside of the wearable, inside of the wearable, or preferably between two layers of the wearable, advantageously preventing the catching or tangling of electrode leads. To accommodate the stretching or resizing of the wearable without the electrode leads yanking or pulling on the electrodes or other connections, the electrode leads may be folded or coiled within the wearable, or may be made of a stretchable or mechanically extensible electrical conductor, such as the type disclosed is U.S. Pat. No. 2,697,157, herein incorporated by reference. In some embodiments, the electrode connections may be made by alternating layers of conductive and insulating material within the wearable, by screen printing connections onto the fabric of the wearable, by including an integral connecting mechanism, or by having conductive fibers woven into the wearable.

In the preferred embodiments of the present invention, the wearable additionally comprises a connector for attaching the apparatus to a data acquisition system. In such embodiments, a plurality of electrode leads or other sensor wires are yoked into the connector for easy connection to a tether, bridge, or radio data transmission device.

The sensors of the apparatus of the present invention may be secured to the wearable by friction fit, threads, grommet, snap, twist-and-lock connector, magnets, or other methods apparent to those skilled in the art. The method for connecting the sensors to the wearable may be mechanical, electrical, or both. In some embodiments, the sensors may be permanently sewn into the garment, or secured thereon by glue, cement, stitching, epoxy, or any other means of permanent attachment known in the art. Sensors may also be fixed to the wearable by tape or temporary adhesive.

In some embodiments, sensors may be held in place upon the skin with a thin film of tape or other temporary adhesive that contacts the skin surface, in addition to being held in place by the wearable. The holding capability of the wearable is thus augmented by the holding capability of the tape or adhesive.

In some embodiments of the present invention, one or more of the electrodes is preferably reinforced within the wearable through the use of a stiffener or stiffening ring used at the place the sensor is integrated into the wearable. Each of the stiffener locations may or may not have sensors during monitoring or acquisition. Preferably, each sensor may be integrated or secured with or without the stiffener. The stiffener or stiffening ring may comprise a hard or stiff material impregnating the wearable, or may consist of a separate hard or stiff piece of material that is installed or affixed in or on the wearable, either permanently, semi-permanently, or impermanently.

In some embodiments of the present invention, the electrical pathways are electrically shielded from large defibrillator voltages and smaller voltages, for example, voltages induced by electromagnetic interference from surrounding equipment, lights, etc., both of which would degrade the biopotential signal. The electrical pathways within the flexible substrate may be longitudinally enclosed with a conductive layer of shielding, such as metal or foil, extending from the electrode connector to the output plug at the opposite end of the electrode harness. Each individual electrical pathway may be shielded.

In some embodiments, the material of the electrode harness of the present invention preferably comprises electrode connectors to mechanically and electrically connect the electrode harness with various types of electrodes. The electrical connectors can be releasable, lockable, non-releasable or permanent connections. Releasable connectors are those connectors to which electrodes can be connected or disconnected with little or no effort. Traditional button type gel-electrodes use such connectors. The drawback of these types of connectors is that sometimes they become inadvertently disconnected through motion of the subject or by external forces on the materials or leads attached to such connectors. In addition, like the disposable or single use electrodes, the electrode harness may also be designed or intended to be for one use only. Lockable connectors are connectors that can be removed from the electrode but only upon the application of forces greater than those normally encountered during the application for which the connector is being used or where there is some mechanical mechanism that needs to be activated or opened in order to release the electrode. Non-releasable connectors are those connectors, which after attaching to an electrode do not release the electrode unless the connector is somehow destroyed. Permanent connections are where the electrode is glued, welded, soldered, cemented, brazed or permanently attached by some means to the material of the electrode harness. Where connectors are used, the connectors may comprise clips, snaps, and both male and female connectors. The connectors may also include any other device for mechanically and electrically connecting the electrode to the electrode harness.

The electrodes used with the electrode harness and methods of the present invention include, but are not limited to, gel-type electrodes and dry electrodes. The gel-type electrodes usually comprise a sensing element and a conductive gel for transmitting the signal between the subject's skin and the sensing element. Most preferably, however, dry electrodes are used. The dry electrodes may comprise a plurality of anchoring elements for detecting physiological signals below the surface of the skin as a sensing element. Dry physiological recording electrodes of the type are described in U.S. Pat. No. 6,782,283, which is herein incorporated by reference. Dry electrodes provide the advantages of not having any gel that could dry out and increase contact impedance, obviate the need to abrade or clean skin at the electrode site, and are capable of being applied on moderately hairy areas. Alternatively, the subject's skin may be mechanically abraded, or an amplified electrode may be used. Preferably, the plurality of electrodes includes at least one signal electrode and one reference electrode. The plurality of electrodes may include electrodes of different types; for example, it may include a mix of one or more conductive gel-type electrodes and one or more dry electrodes. The plurality of electrodes can be of any shape known to be useful to those skilled in the art. For example, the electrodes can be circular or non-circular in shape, and may differ from each other in shape and size.

In some embodiments of the present invention, the interface between the wearable and an affixed or embedded electrode may consist of a hole in the material of the wearable through which the electrode partially fits as a button. In such an implementation, the electrical connector side of the electrode may protrude completely through the wearable, allowing electrode lead connections to be made on the outside of the wearable, or the electrode may only partially or incompletely protrude, as through only an inner layer of a multi-layer wearable, wherein electrode lead connections may be made within the wearable.

The electrode harness of the present invention is preferably connected to a tether or a wireless transmitter or transceiver by a lead connector. A lead connector functions to connect the electrical pathways from the material of the electrode harness into the tether or wireless system via a standard electrical configuration. The tether is a wired connector to connect the electrode harness to a monitor, processor or other device, which preferably enables the subject or the subject's health care provider to utilize the biopotential signals. The wireless transmitter or transceiver receives the signals from the electrodes, and comprises a radio, ultrasound, infrared or other transmitter. Optionally, the transceiver operates according to Bluetooth specifications. Preferably, the transceiver operates according to an appropriate and approved communications/electronics specification, for example, a standard approved by the FCC. The transmitter or transceiver can include, but is not limited to, various components such as electrode signal channels, a multiplexer, analog to digital converter(s), a controller, a radio, a battery, and the like. Additional, fewer or different components can be used. Preferably, the electrode harness of the present invention is advantageously adaptable to any biopotential signal acquisition system.

In one embodiment, the transmitter operates in a manner that minimizes introducing undesired noise or signals. The selected signals are transmitted as radio or other signals. Various formats can be used for transmission of signals. Such formats include, but are not limited to Bluetooth, TCP/IP, or other formats. The controller controls the signal acquisition and signals. The transmitted signals comprise data representing the biopotential signals received from the electrodes. In one embodiment, the transmitter also receives control information from the receiver, such as instructions to resend signals.

The transmitter is positioned near, or attached to, the monitored subject. Preferably, the wearable of the present invention provides a pocket, strap, clip, hook and loop strip, or connector for the attachment of the transmitter to the wearable. The transmitter may alternatively be attached to the monitored subject through the use of an appendage band elsewhere on the subject (e.g. arm, leg, wrist, ankle, etc.) or in close proximity to the subject.

In one embodiment, the transmitter is removable from the electrical pathway leading to the electrodes. Clips, plugs, clips, screws, bolts, latches, adhesive, or other devices may be used to releasably connect the transmitter to the electrical pathway. Electrical contact is provided by connectors operable to withstand electrical energy produced by a defibrillator. These connectors may also provide the physical connection between the transmitter and the electrical pathways mentioned above. The transmitter may be removed for replacing or recharging the battery, and/or there is a mechanism such as a plug used to recharge the battery without removal. The battery or transmitter, like the electrode harness and the electrodes, can be used for multiple days or multiple times and is separately disposable to avoid costly replacement of the entire system.

The receiver comprises a radio, infrared, ultrasound or other receiver. An application specific integrated circuit, digital signal processor or other circuit for receiving signals from the transmitter, decoding the received signals, and generating representative electrode signals may be used. In one embodiment, the receiver comprises a transceiver for two-way communication with the transmitter. For example, a transceiver operable pursuant to the Bluetooth specification is provided.

The radio demodulates the received signals for identifying digital data representing the electrode signals. In various embodiments, the radio also includes a modulator for transmitting control information.

The biopotential monitor comprises one or more of a bedside monitor, a transport monitor or a discrete (i.e.

diagnostic) monitor. Bedside and transport monitors may be used for continuous monitoring.

FIG. 1 shows a schematic view of a subject wearing a biopotential measurement system with one embodiment of the electrode harness of the present invention. This particular embodiment of the biopotential measurement system comprises a wearable 12 (illustrated here as an elastic, form-fitting tube garment) into which have been embedded electrodes 13, and transceiver 14, which is worn by the subject 10 in a pocket 15 in the wearable 12. The transceiver is detachably connected to the wearable via a connector (not shown). The wearable 12 further comprises electrical pathways 16, which carry the biopotential signals from the electrodes 13 to the transceiver 14. The transceiver 14 may transmit acquired biopotential data to a receiver 17 for real-time viewing and storage on a computer 18, and/or may store acquired data on a memory inside the transceiver 14. In various additional embodiments of the present invention, the wearable 12 may be a belt, strap, shirt, bra, gown, undergarment, high-waisted pant, or other garment or garment-like device. The apparatus can be used to monitor the subject, the fetus, or both. In the illustrated embodiment of the invention, fetal and/or maternal electrocardiograms are non-invasively acquired by placing the wearable around a torso of the pregnant subject, the wearable having a plurality of dry electrodes and a connector, connecting the wearable, via the connector, to an electronic device capable of recording or transmitting electrical signals received from the plurality of dry electrodes, and differentiating between the electrocardiogram of the subject and the electrocardiogram of the fetus.

Figure 2:
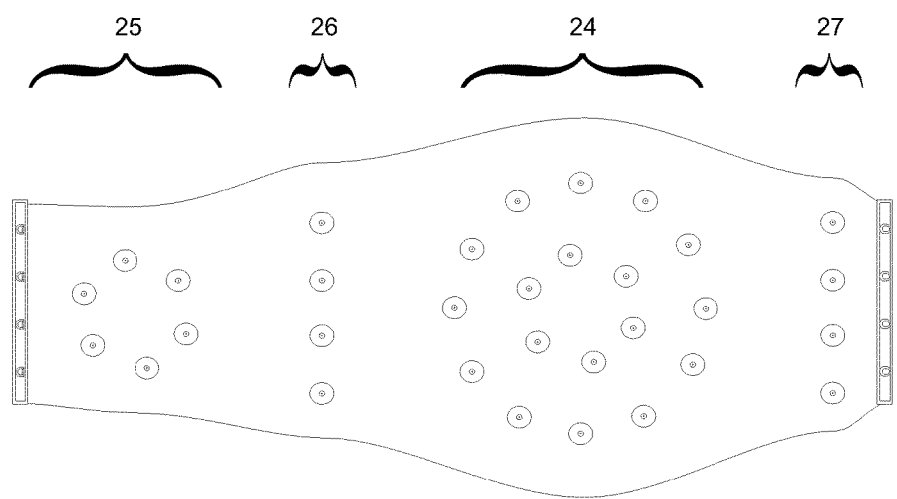
FIG. 2. Schematic view of one arrangement of electrodes in one embodiment of the electrode harness of the present invention.

FIG. 2 shows a schematic view of one arrangement of electrodes in one embodiment of the electrode harness of the present invention. A group of electrodes 24 is arranged into two concentric rings, this group being intended to be positioned over the front of the torso once the wearable that includes the electrodes is worn by the subject. Linear arrangements of electrodes 26, 27 are intended to be respectively positioned over the right and left sides of the subject's torso once the wearable that includes the electrodes is worn by the subject. An additional ring of electrodes 25 is intended to be positioned on the back of the subject's torso once the wearable that includes the electrodes is worn by the subject. The illustrated embodiment is one example of an electrode arrangement that allows capture of the maternal ECG and fetal ECG in at least several electrical axes, thereby accommodating movement of the subject and fetus.

Figure 3A:
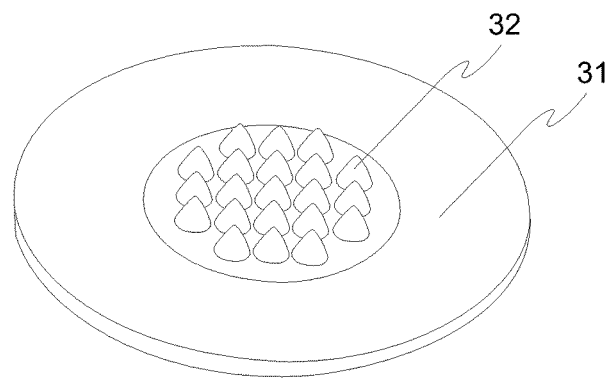
FIG. 3. Schematic views of the dry electrode used in the some embodiments of the present invention. 3a shows the proximal side of the dry electrode with anchoring members; 3b shows the distal side with a snap connector; 3c shows the distal side with a semi-permanent or permanent connector.
Figure 3B:
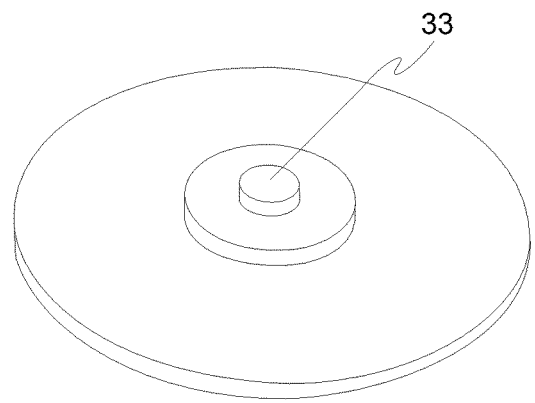

FIG. 3 shows schematic views of a dry electrode used in some embodiments of the present invention. The wearable 12 of FIG. 1 advantageously employs dry physiologic electrodes to provide a large number of electrodes while minimizing or eliminating the steps of skin abrasion and cleaning. FIG. 3a shows the proximal side of the dry electrode 31 with anchoring members 32. Anchoring members 32 promote sustained lower-impedance electrical contact with the skin and comfortably help to maintain electrode placement. FIG. 3b shows the distal side of the dry electrode with a snap connector 33. In some embodiments, electrode leads may be connected to the dry electrode via the snap connector; in other embodiments, the electrode may be attached to leads by other means. In embodiments of the invention where the wearable including the electrodes is intended to be disposable, the electrodes are optionally permanently attached to the electrode leads. In other embodiments where the wearable is intended to be disposable but the electrodes are intended to be detachable from the wearable, the detachable electrode—lead connector may be preferred, which may include a snap, clips, plug, screw, bolt, latch, or adhesive.

Figure 3C:
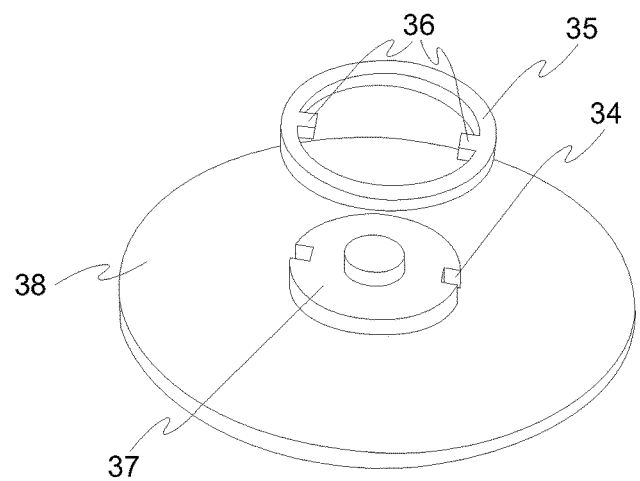

FIG. 3c shows the distal side with one type of semi-permanent or permanent connector for attaching the electrode to the wearable. Connector ring 35 includes keys 36. When the electrode is placed inside of the wearable, proximal to the skin surface of the patient, with raised area of the electrode protruding distally through a hole in the wearable, the hole being of diameter larger than the diameter of raised area 37 but smaller than diameter of connector ring 35, then the connector ring 35 is fitted to the electrode on the outside of the wearable to the distal side of the electrode, such that the keys 36 of the connector ring 35 fit to keyholes 34 of the electrode. The connector ring 35 may be twisted to secure it to the electrode either permanently or semi-permanently. Other embodiments of a permanently or semi-permanently attachable electrode, not illustrated, follow similar design but may use screwthreading or tapered clips in lieu of keys 36 and keyholes 34. Still other embodiments may incorporate electrode attachment methods disclosed in U.S. patent application Ser. No. 10/988,358, which is herein incorporated by reference, in particular those illustrated in FIGS. 8 through 11 of that application.

Figure 4A:
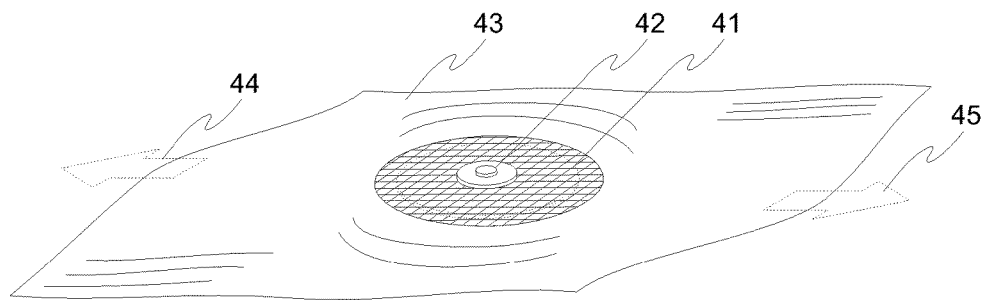
FIG. 4. Schematic views of a dry electrode in the electrode harness of the present invention both with (a) and without (b) a stiffening ring used in the some embodiments of the present invention.
Figure 4B:
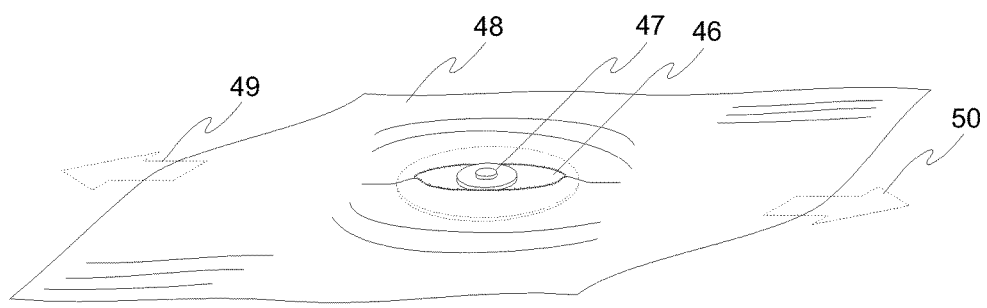

FIG. 4a and FIG. 4b illustrate the usefulness of a stiffening ring in some embodiments of the present invention. FIG. 4a shows a schematic view of a dry electrode with a stiffening ring. In embodiments that use a stiffening ring, stiffening ring 41, made from an electrically insulating material such as plastic, is either placed in between electrode 42 and wearable 43, proximal to the subject within the wearable but on the distal side of the electrode, or is impregnated within the material of the wearable, or is adhered or otherwise attached to one or both sides of the wearable. The electrode is permanently or semi-permanently attached to the wearable by the means described above or by other means. Without the stiffening ring, as shown in FIG. 4b, when forces 49 and 50 stretch the material of the wearable 48, the hole 46 through which the electrode 47 protrudes becomes elongated and frayed, and the material of the wearable 48 may contort into hills and valleys around the site of the hole 47. Each of these effects may have negative consequences on the proper positioning of the electrode 47 and the gentle compression of the electrode 47 onto the surface of the skin as exerted by the material of the wearable 48. By contrast, in FIG. 4a, the forces 44 and 45 that stretch the material of the wearable 43 do not pull apart the wearable at the site of the electrode 42 thanks to the augmentation of the material of the wearable by the stiffening ring 42. The stiffening ring 42 thus promotes the maintenance of electrode placement and compression on the electrode site and the electrode's position with respect to other electrodes similarly affixed to the wearable.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:
1. An apparatus for non-invasively acquiring the electrocardiogram of a fetus comprising:
    a wearable worn completely about a torso of a pregnant subject, the torso having a front, a back, and two sides,
    a plurality of dry ECG electrodes affixed or embedded in the wearable, such that the wearable when properly worn positions at least eight dry ECG electrodes about the torso of the pregnant subject, at least two dry ECG electrodes on each of the sides, the back, and the front of the torso of the subject, and at least one of the dry electrodes is secured to the wearable by a snap connector, and a plurality of connectors providing an electrical pathway from each of the plurality of dry ECG electrodes wherein the dry ECG electrodes are capable of being connected to an electronic device which is capable of modifying and/or re-transmitting electrical signals or modified electrical signals received from the plurality of dry ECG electrodes.

2. The apparatus of claim 1, where at least one of the dry electrodes has an anchoring member to promote sustained lower-impedance electrical contact with the skin and comfortably help to maintain electrode placement.

3. The apparatus of claim 1, where the dry electrodes are reinforced by a stiffener at their place of attachment to the wearable.

4. The apparatus of claim 1, where the wearable is an elastic garment.

5. The apparatus of claim 1, where the wearable is secured about the torso of the subject by hook-and-loop fasteners.

6. An apparatus for non-invasively acquiring the electrocardiogram of a fetus comprising a wearable worn completely about the torso of a pregnant subject, the torso having a front, a back, and two sides, a plurality of dry ECG electrodes affixed or embedded in the wearable, such that the wearable when properly worn positions at least four dry ECG electrodes about the torso of the pregnant subject, at least one dry ECG electrode on each of the sides, the back, and the front of the torso of the subject, and at least one of the dry electrodes is secured to the wearable by a friction fit connector, and a plurality of connectors providing an electrical pathway from each of the plurality of dry ECG electrodes wherein the dry ECG electrodes are capable of being connected to an electronic device capable of modifying and/or re-transmitting electrical signals or modified electrical signals received from the plurality of dry ECG electrodes.

7. The apparatus of claim 6, where at least one of the dry electrodes has an anchoring member to promote sustained lower-impedance electrical contact with the skin and comfortably help to maintain electrode placement.

8. The apparatus of claim 6, where the dry electrodes are reinforced by a stiffener at their place of attachment to the wearable.

9. The apparatus of claim 6, where the wearable is an elastic garment.

10. The apparatus of claim 6, where the wearable is secured about the torso of the subject by hook-and-loop fasteners.

* * * * *